United States Patent [19]

Leppard et al.

[11] Patent Number: 4,518,679

[45] Date of Patent: May 21, 1985

[54] COLOR-PHOTOGRAPHIC RECORDING MATERIAL

[75] Inventors: David G. Leppard, Marly; Jean Rody, Riehen, both of Switzerland

[73] Assignee: Ciba-Geigy AG, Basel, Switzerland

[21] Appl. No.: 557,366

[22] Filed: Dec. 2, 1983

[30] Foreign Application Priority Data

Dec. 3, 1982 [CH] Switzerland .................. 7046/82

[51] Int. Cl.$^3$ .................. G03C 7/40; G03C 7/26
[52] U.S. Cl. .................. 430/372; 430/505; 430/551
[58] Field of Search .................. 430/372, 551, 505

[56] References Cited

U.S. PATENT DOCUMENTS

| | | | |
|---|---|---|---|
| 3,859,293 | 1/1975 | Murayama et al. | 524/99 |
| 3,941,744 | 3/1976 | Murayama et al. | 524/100 |
| 4,110,334 | 8/1978 | Mayer et al. | 524/95 |
| 4,268,593 | 5/1981 | Leppard et al. | 430/512 |
| 4,452,884 | 6/1984 | Leppard | 430/961 |

*Primary Examiner*—J. Travis Brown
*Attorney, Agent, or Firm*—Wenderoth, Lind & Ponack

[57] ABSTRACT

A color-photographic recording material which, in at least one light-sensitive silver halide emulsion layer, one intermediate layer and/or one protective layer, contains, as a stabilizer, at least one polyalkylpiperidine compound of the formula I or II $$\left[ \begin{array}{c} TH_2C \quad CH_3 \\ \diagup \quad \diagdown \\ T_1-N \qquad\qquad X-Y-\overset{O}{\underset{\|}{C}}\!\!-\!\!A \\ \diagdown \quad \diagup \\ TH_2C \quad CH_3\,T \end{array} \right]_m \quad (I)$$

-continued $$\left[ \begin{array}{c} CH_3 \quad CH_2T \\ \diagup \quad \diagdown \\ W \qquad\qquad N-Z-Y-\overset{O}{\underset{\|}{C}}\!\!-\!\!A \\ \diagdown \quad \diagup \\ T\,CH_3 \quad CH_2T \end{array} \right]_m \quad (II)$$

in which m is the numbers 1 or 2 and, if m=1, A is a group of the formula $$-(CH_2)_{\overline{a}}(\overset{G}{\underset{E}{C}})_{\overline{n}}(CH_2)_{\overline{p}} \!\!-\!\! \begin{array}{c} R_1 \\ \diagup \diagdown \\ \diagdown \diagup \\ R_3 \end{array} \begin{array}{c} OH \\ R_2 \end{array}$$

and, if m=2, A is a group of the formula $$\begin{array}{c} \diagdown \quad CH_2\!-\! \\ \phantom{xx}C \\ \diagup \quad \diagdown \\ R_4\,R_3 \end{array} \begin{array}{c} R_1 \\ \diagup \diagdown \\ \diagdown \diagup \\ \end{array} \begin{array}{c} OH \\ R_2 \end{array}$$

Color images which are obtained by image-wise exposure and development of this color-photographic recording material, display good stability towards the action of visible and ultraviolet light.

Reference is made to the description in respect of the meanings of the substituents and symbols in the formulae I and II.

14 Claims, No Drawings

COLOR-PHOTOGRAPHIC RECORDING MATERIAL

The present invention relates to a colour-photographic recording material containing, as a stabilizer, a specific polyalkylpiperidine spiro compound in at least one light-sensitive silver halide emulsion layer and/or in at least one of the conventional auxiliary layers.

As sterically hindered amines, polyalkylpiperidines are generally known as light stabilizers for organic materials, in particular for polymers. The use of such polyalkylpiperidines as agents against the fading of colour photographs has also already been suggested in German Offenlegungsschrift 2,126,187. The use of specific polyalkylpiperidine derivativies containing at least one phenol group as light stabilizers for colour photographs has also been suggested in European Patent Application 11,051. These are polyalkylpiperidine esters of hydroxybenzylmalonic acids.

In following up this research work further, it has been found that compounds containing at least one sterically hindered phenol group and at least polyalkylpiperidine spiro group in their molecule display a surprisingly improved stabilizing action.

The present invention relates, therefore, to a colour-photographic recording material which, in at least one light-sensitive silver halide emulsion layer, one intermediate layer and/or one protective layer, contains, as a stabilizer, at least one polyalkylpiperidine compound, wherein the polyalkylpiperidine compound has one of the formulae I or II

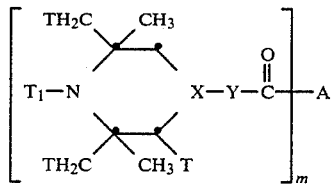

(I)

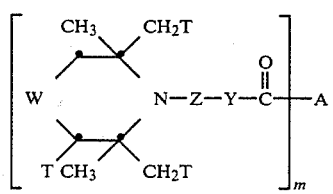

(II)

in which m is the numbers 1 or 2, if m=1, A is a group of the formula

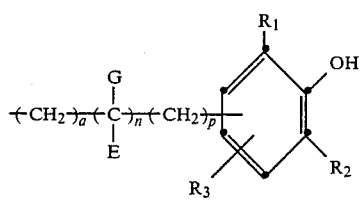

and, if m=2, A is a group of the formula

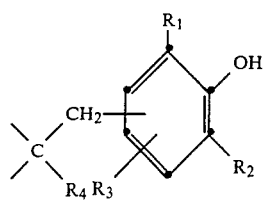

in which $R_1$ is hydrogen, $C_1-C_{12}$-alkyl, $C_5-C_8$-cycloalkyl, $C_7-C_9$-phenylalkyl, phenyl or $C_7-C_{10}$-alkylphenyl, $R_2$ is $C_1-C_8$-alkyl, $C_5-C_8$-cycloalkyl, $C_7-C_9$-phenylalkyl, phenyl or $C_7-C_{10}$-alkylphenyl, $R_3$ is hydrogen or methyl, $R_4$ is hydrogen, $C_1-C_{12}$-alkyl, allyl, benzyl, cyclohexyl or a group

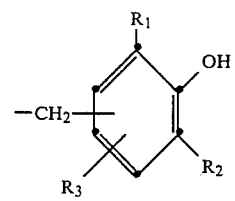

G is hydrogen or a group

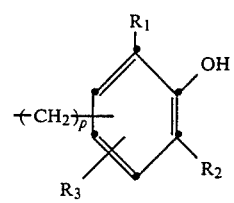

E is hydrogen, methyl, —CN, —$COR_5$ or —$COOR_5$, $R_5$ being $C_1-C_8$-alkyl or $C_3-C_4$-alkoxyalkyl, and n and p independently of one another are the numbers 0 or 1 and a is the numbers 0, 1 or 2, Y is —O— or —N($R_6$)—, $R_6$ being hydrogen, $C_1-C_{18}$-alkyl, $C_3-C_{12}$-alkenyl, $C_5-C_8$-cycloalkyl, phenyl, $C_7-C_{14}$-alkaryl, $C_7-C_{14}$-aralkyl or $C_3-C_4$ alkoxyalkyl, Z is a group

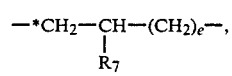

in which $R_7$ is hydrogen, methyl, ethyl, phenoxymethyl, phenyl or —$OR_8$, but is only —$OR_8$ if e is 1, and in which $R_8$ is hydrogen or —COL, L is $C_1-C_4$-alkyl, e is the number 0 or 1 and the *C is attached at the piperidine nitrogen, T is hydrogen or methyl, $T_1$ is hydroxyl, $C_1-C_{12}$-alkyl, $C_3-C_6$-alkenylmethyl or $C_3-C_4$-alkynylmethyl and $C_7-C_{14}$-aralkyl, glycidyl, $C_1-C_4$-alkyl which is substituted by halogen, cyano, —$COOR_9$ or —$CON(R_{10})$ ($R_{11}$), a group —$COR_{12}$, —$COOR_9$ or —$CON(R_{10})$ ($R_{11}$) or a group —$CH_2$—$CH(R_{13})$—$OR_{14}$, —$SOR_{15}$, —$SO_2R_{15}$, —$OR_9$ or —$OOCR_{12}$ in which $R_9$ is $C_1-C_{12}$-alkyl, allyl, cyclohexyl or benzyl, $R_{10}$ is $C_1-C_{12}$-alkyl, allyl, cyclohexyl, benzyl, phenyl or $C_7-C_{10}$-alkylphenyl and $R_{11}$ is hydrogen, $C_1-C_{12}$-alkyl, allyl, cyclohexyl or benzyl, or $R_{10}$ and $R_{11}$, together with the N atom to which they are attached, form a 5-membered or 6-membered heterocyclic ring, $R_{12}$ is hydrogen, $C_1-C_{12}$-alkyl, $C_2-C_6$-alkenyl, chloromethyl, $C_5-C_8$-cycloalkyl, $C_7-C_{14}$-aralkyl, phenyl, $C_7-C_{10}$-alkylphenyl or phenyl, phenylmethyl or phenylethyl which is substituted by one or two $C_1$–$C_4$-alkyl groups and by one hydroxyl group, $R_{13}$ is hydrogen, $C_1$–$C_4$-alkyl, $C_3$–$C_4$-alkoxyalkyl, phenyl or phenoxymethyl, $R_{14}$ is hydrogen, $C_1$–$C_{12}$-alkyl or a group —$COR_{12}$ or —$CON(R_{10})(R_{11})$ and $R_{15}$ is $C_1$–$C_{12}$-alkyl, phenyl or $C_7$–$C_{10}$-alkylphenyl, or $T_1$ is a group of the formula

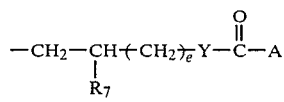

or of the formula

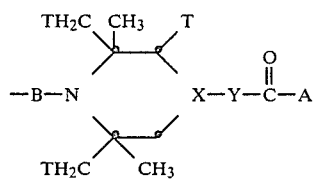

in which B is a group $C_rH_{2r}$ in which r is a number from 2 to 12, or is $C_4$–$C_8$-alkenylene, $C_4$–$C_8$-alkynylene, phenylene, xylylene, bitolylene, $C_5$–$C_{12}$-cycloalkylene or a group —CONH—$B_1$—NHCO— in which $B_1$ is a group $C_rH_{2r}$, phenylene, naphthylene, tolylene or a group of the formulae

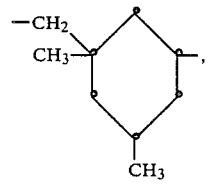

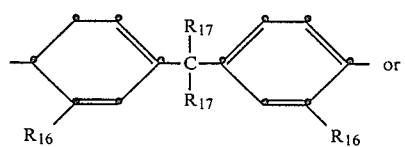

in which $R_{16}$ is hydrogen or methyl and $R_{17}$ is hydrogen, methyl or ethyl, X is one of the groups

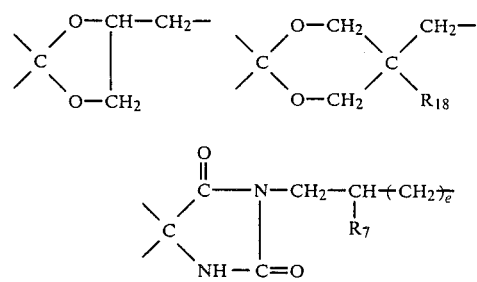

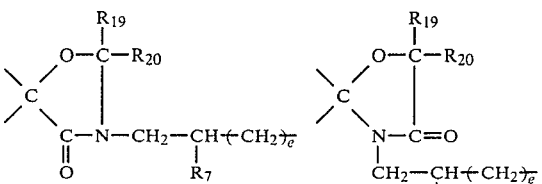

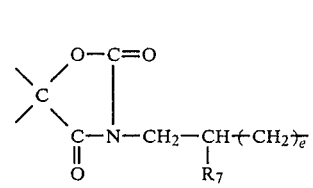

and W is one of the groups

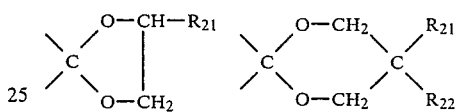

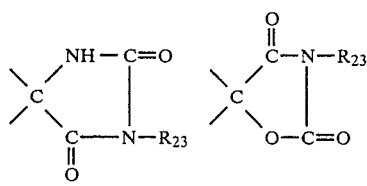

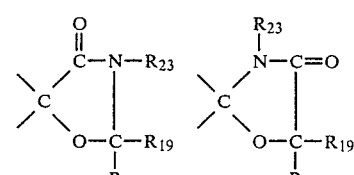

in which $R_{18}$ is methyl or ethyl, $R_{19}$ is hydrogen, $C_1$–$C_{12}$-alkyl, $C_5$–$C_8$-cycloalkyl or $C_7$–$C_{14}$-aralkyl, $R_{20}$ is $C_1$–$C_{12}$-alkyl, $C_5$–$C_8$-cycloalkyl or phenyl, or $R_{19}$ and $R_{20}$, together with the C atom to which they are attached, form a $C_5$–$C_{12}$ cycloalkane or alkylcycloalkane ring, $R_{21}$ is hydrogen, $C_1$–$C_{12}$-alkyl or a group of the formula —$CH_2$—$OCOR_{24}$ in which $R_{24}$ is hydrogen, $C_1$–$C_4$-alkyl, $C_2$–$C_6$-alkenyl, cyclohexyl, phenyl, benzyl or chloromethyl, or is a group —$CH_2$—O—$SO_2R_{27}$ in which $R_{27}$ is methyl, phenyl or p-tolyl, or is one of the groups

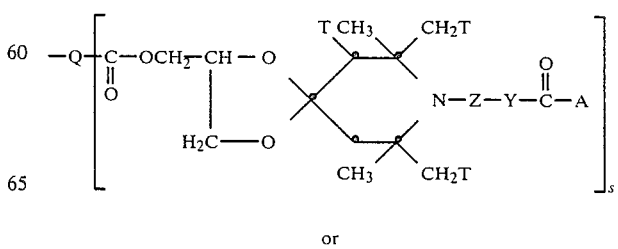

or

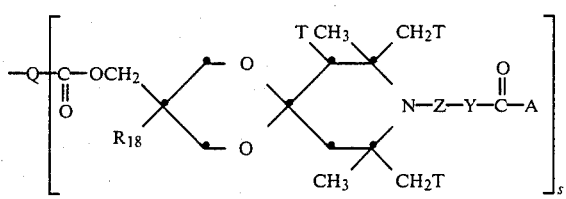

in which s is the number 1, 2 or 3, and, if s=1, Q is as defined above for B, if s=2, Q is a trivalent radical of the formulae

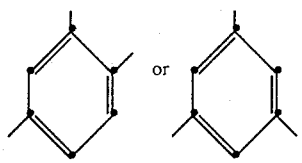

and, if s=3, Q is a tetravalent radical of the formulae

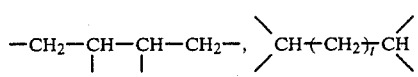

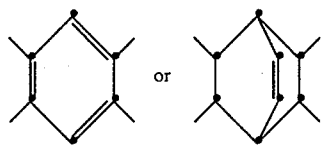

in which t is the numbers 1 to 8, and $R_{21}$ additionally is also a group of the formula $-CH_2O-S-O-R_{25}$ in which $R_{25}$ is $C_1-C_4$-alkyl, p-tolyl or phenyl, or is a group of the formula $-CH_2-CO-NHR_{26}$ in which $R_{26}$ is hydrogen or $C_1-C_4$-alkyl, $R_{22}$ is hydrogen or $C_1-C_4$-alkyl and $R_{23}$ is hydrogen, $C_1-C_{12}$-alkyl, $C_3-C_4$-alkoxyalkyl, $C_5-C_8$-cycloalkyl, allyl or benzyl, and, if m is 1, W can additionally also be a group of the formula

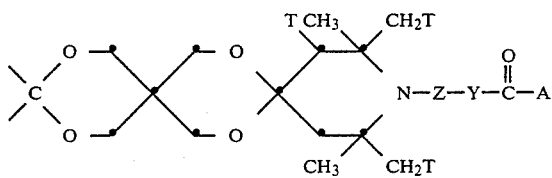

the radicals and symbols mentioned several times always being as defined initially.

If any substituents are alkyl, this is a linear or branched alkyl group. If the substituents are $C_1-C_4$-alkyl, this is methyl, ethyl, n-propyl, isopropyl, n-butyl, sec.-butyl or tert.-butyl. If they are $C_1-C_8$-alkyl, n-pentyl, 2,2-dimethylpropyl, n-hexyl, 2,3-dimethylbutyl, n-octyl or 1,1,3,3-tetramethylbutyl, for example, are also suitable. If they are $C_1-C_{12}$-alkyl, this can additionally also be, for example, nonyl, decyl, undecyl and dodecyl. As $C_1-C_{18}$-alkyl, $R_6$ is additionally, for example, tetradecyl, hexadecyl, heptadecyl or octadecyl.

As substituted $C_1-C_4$-alkyl, $T_1$ can be, for example, substituted methyl, ethyl substituted in the 1-position or 2-position, propyl substituted in the 1-, 2- or 3-position or n-butyl substituted in the 1-, 2-, 3- or 4-position. It can also be substituted tert.-butyl or sec.-butyl.

If any substituents are $C_5-C_8$-cycloalkyl, this can be, for example, cyclopentyl, cyclohexyl, cycloheptyl, α-methylcyclohexyl, cyclooctyl or dimethylcyclohexyl.

If $R_{19}$ and $R_{20}$, together with the C atom to which they are attached, form a $C_5-C_{12}$ cycloalkane or alkylcycloalkane ring, this is, for example, cyclopentane, cyclohexane, cycloheptane, cyclooctane, cyclodecane, cyclododecane, methylcyclohexane or dimethylcyclohexane.

Examples of $R_1$ and $R_2$ as $C_7-C_9$-phenylalkyl are benzyl, phenylethyl or phenylpropyl. If $T_1$, $R_6$, $R_{12}$ and $R_{19}$ are $C_7-C_{14}$-aralkyl, this is, additionally also phenylbutyl or naphthylmethyl, for example.

Possible examples of $R_1$, $R_2$, $R_{10}$, $R_{12}$ and $R_{15}$ as $C_7-C_{10}$-alkylphenyl are tolyl, xylyl, isopropylphenyl, tert.-butylphenyl or diethylphenyl.

Examples of $R_6$, $R_{12}$ and $R_{24}$ as $C_3-C_6$-alkenyl, and of $T_1$ as $C_3-C_6$-alkenylmethyl, are allyl, methallyl, dimethylallyl or 2-hexenyl; as $C_2-C_6$-alkenyl, $R_{12}$ and $R_{24}$ can additionally also be vinyl.

As $C_3-C_{12}$-alkenyl, $R_6$ can additionally also be 2-octenyl, 2-decenyl or 2-dodecenyl.

Examples of $T_1$ as $C_3-C_4$-alkynylmethyl are propargyl, n-but-4-inyl or n-but-3-inyl. Propargyl is preferred.

If $R_6$ is $C_7-C_{14}$-alkaryl, it can be: phenyl substituted by $C_1-C_4$-alkyl, such as p-tolyl, 2,4-dimethylphenyl, 2,6-dimethylphenyl, 2,4-diethylphenyl, 2,6-diethylphenyl, 4-tert.-butylphenyl, 2,4-di-tert.-butylphenyl or 2,6-di-tert.-butylphenyl. 2,4-di-tert.-butylphenyl and 2,4-dimethylphenyl are preferred.

Examples of $R_5$, $R_6$, $R_{13}$ and $R_{23}$ as $C_3-C_4$-alkoxyalkyl are ethoxymethyl, 2-methoxyethyl or 2-ethoxyethyl.

If B is $C_4-C_8$-alkenylene, it is, for example, but-2-en-1,4-ylene.

If B is $C_4-C_8$-alkynylene, it is, for example, but-2-in-1,4-ylene.

If B is $C_5-C_{12}$-cycloalkylene, it is, for example, cyclopentylene, cyclohexylene, cyclooctylene, cyclodecylene or cyclododecylene. Cyclohexylene is preferred. Examples of $R_{12}$ as phenyl, phenylmethyl or phenylethyl substituted by 1 or 2 $C_1-C_4$-alkyl groups and 1 hydroxyl group are 3,5-dimethyl-4-hydroxyphenyl, 3,5-di-tert. butyl-4-hydroxyphenyl, 3,5-dimethyl-4-hydroxyphenyl, 3,5-dimethyl-4-hydroxybenzyl, 3,5-di-tert.butyl-4-hydroxybenzyl or 2-(3,5-di-tert.-butyl-4-hydroxyphenyl)-ethyl.

If any substituents are halogen, this is, for example, bromine, iodine and especially chlorine.

Compounds which are of particular interest as stabilizers are those of the formulae III and IV

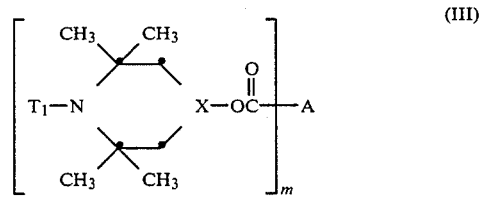

(III)

-continued

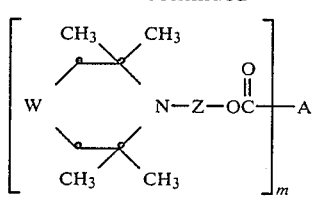
(IV)

in which m is the numbers 1 or 2, if m=1, A is a group of the formula

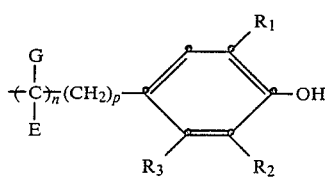

and, if m=2, A is a group of the formula

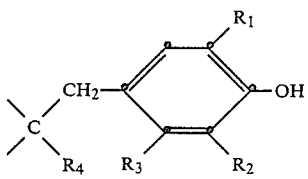

in which $R_1$ is $C_1$-$C_4$-alkyl, $R_2$ is hydrogen or $C_1$-$C_4$-alkyl, $R_3$ is hydrogen or methyl, $R_4$ is hydrogen, $C_1$-$C_4$-alkyl or a group

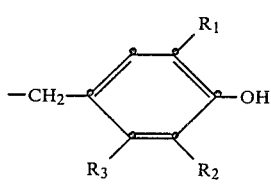

G is hydrogen or a group

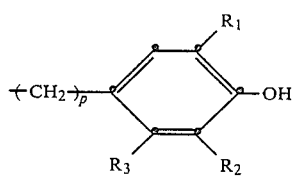

E is hydrogen, methyl, —CN or —COCH$_3$ and n and p independently of one another are the numbers 0 or 1, Z is a group

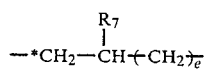

in which $R_7$ is hydrogen, methyl, ethyl, phenoxymethyl and phenyl, e is the numbers 0 or 1 and the *C is attached at the piperidine nitrogen, $T_1$ is hydroxyl, $C_1$-$C_4$-alkoxy, acetoxy, $C_1$-$C_4$-alkyl, $C_3$-$C_4$-alkenylmethyl, propargyl, glycidyl, benzyl, methyl or ethyl which is substituted by —COOR$_9$, a group —COR$_{12}$, —COOR$_9$ or —CON(R$_{10}$) (R$_{11}$), or a group —CH$_2$—CH(R$_{13}$)—OR$_{14}$ in which $R_9$ is $C_1$-$C_8$-alkyl, allyl or cyclohexyl, $R_{10}$ is $C_1$-$C_{12}$-alkyl, cyclohexyl or phenyl, $R_{11}$ is hydrogen or $C_1$-$C_{12}$-alkyl, or $R_{10}$ and $R_{11}$, together with the N atom to which they are attached, form a 6-membered heterocyclic ring, $R_{12}$ is $C_1$-$C_{12}$-alkyl, $C_2$-$C_4$-alkenyl, cyclohexyl, benzyl, phenyl or 2-(3,5-di-tert.-butyl-4-hydroxyphenyl)-ethyl, $R_{13}$ is hydrogen, methyl or phenyl and $R_{14}$ is hydrogen, $C_1$-$C_4$-alkyl or a group —COR$_{12}$ or —CON(R$_{10}$)(R$_{11}$), or $T_1$ is a group of the formula

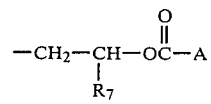

or of the formula

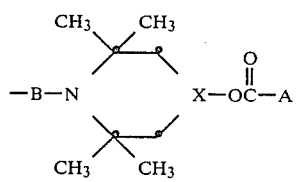

in which B is a group —(CH$_2$)—$_r$ or —CONH—(CH$_2$)—$_r$—NHCO— in which r is the numbers 2 to 8, or is $C_4$-$C_8$-alkenylene, xylylene or bitolylene, X is one of the groups

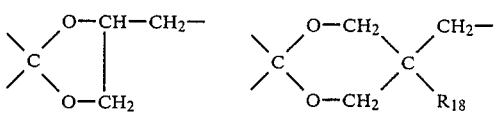

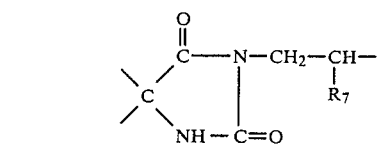

and W is one of the groups

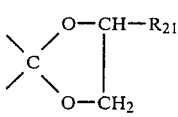 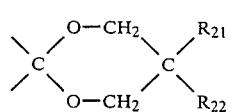

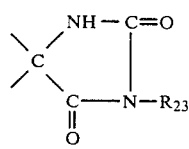

in which $R_{18}$ is methyl or ethyl, $R_{21}$ is hydrogen, $C_1$-$C_8$-alkyl, a group of the formula —CH$_2$—OCOR$_{24}$ in which $R_{24}$ is $C_1$-$C_4$-alkyl, allyl, phenyl or benzyl, or a group of the formula —CH$_2$O—SO$_2$R$_{25}$ in which $R_{25}$ is methyl, phenyl or p-tolyl, $R_{22}$ is hydrogen, methyl or ethyl and $R_{23}$ is hydrogen, $C_1$-$C_8$-alkyl, cyclohexyl, allyl or benzyl, and, if m is 1, W can additionally also be a group of the formula

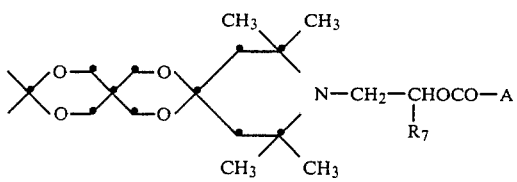 5 the radicals and symbols mentioned several times in this preference always being as defined initially in this preference.

Compounds of the formula III which are preferred as stabilizers are those in which m is the numbers 1 or 2 and, if m=1, A is a group of the formula

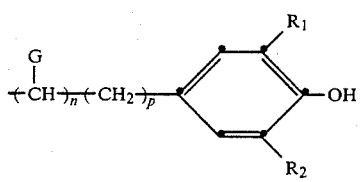

and, if m=2, A is a group of the formula

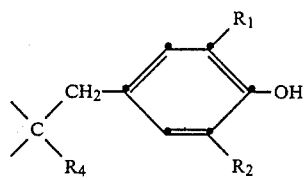

in which $R_1$ is hydrogen, methyl or tert.-butyl, $R_2$ is methyl or tert.-butyl, $R_4$ is hydrogen, $C_1$–$C_4$-alkyl or a group

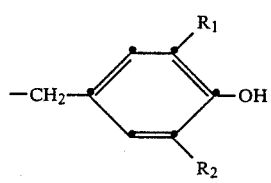

G is hydrogen or a group

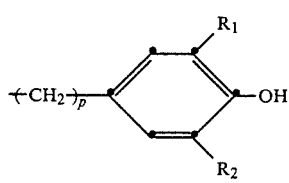

n and p independently of one another are the numbers 0 or 1, $T_1$ is methoxy, methyl, allyl, benzyl, acetyl, acryloyl or a group —$CON(R_{10})(R_{11})$, $R_{10}$ being $C_1$–$C_4$-alkyl, cyclohexyl or phenyl and $R_{11}$ being hydrogen or $C_1$–$C_4$-alkyl, or $T_1$ is a group —$CH_2CH_2$—OCO—A, X is one of the groups

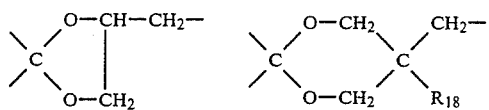

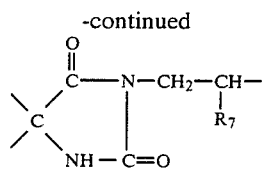

in which $R_7$ is hydrogen, methyl or phenyl and $R_{18}$ is methyl or ethyl, the radicals mentioned several times in this preference always being as defined initially in this preference.

Compounds of the formula IV which are also preferred as stabilizers are those in which m is the number 1 or 2, if m=1, A is a group of the formula

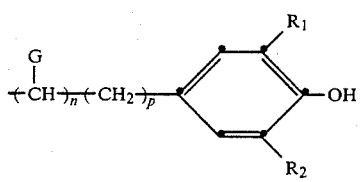

and, if m=2, A is a group of the formula

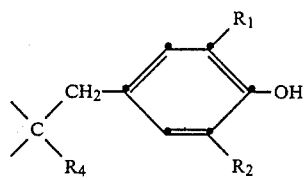

in which $R_1$ is hydrogen, methyl or tert.-butyl, $R_2$ is methyl or tert.-butyl, $R_4$ is hydrogen, $C_1$–$C_4$-alkyl or a group

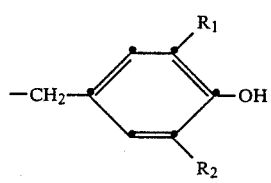

G is hydrogen or a group

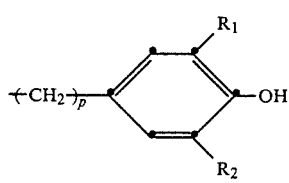

n and p independently of one another are the numbers 0 or 1, Z is a group

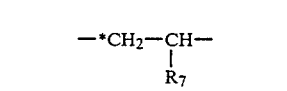

in which $R_7$ is hydrogen, methyl or phenyl and the *C is attached at the piperidine nitrogen, $T_1$ is methoxy, methyl, allyl, benzyl, acetyl, acryloyl or a group —CON $(R_{10})(R_{11})$, —$SOR_{15}$ or —$SO_2R_{15}$, $R_{10}$ being $C_1$–$C_4$-alkyl, cyclohexyl or phenyl, $R_{11}$ being hydrogen or $C_1$-$C_4$-alkyl and $R_{15}$ being methyl, phenyl or p-tolyl, or $T_1$ is a group —$CH_2CH_2$—OCO—A, W is one of the groups

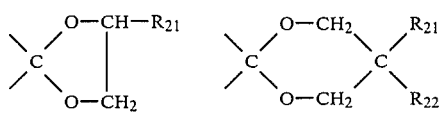

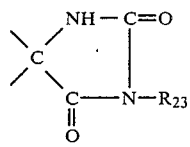

in which $R_{21}$ is hydrogen, $C_1$-$C_8$-alkyl, a group of the formula —$CH_2$—$OCOR_{24}$ in which $R_{24}$ is $C_1$-$C_4$-alkyl, allyl or benzyl, or a group of the formula —$CH_2O$—$SO_2R_{27}$ in which $R_{27}$ is methyl, phenyl or p-tolyl, $R_{22}$ is hydrogen, methyl or ethyl and $R_{23}$ is hydrogen, $C_1$-$C_8$-alkyl, allyl or benzyl, and, if m is 1, W can additionally also be a group of the formula

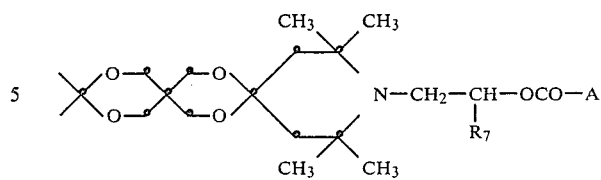

radicals mentioned several times in this preference always being as defined initially in this preference.

The compounds of the formula I and II can be obtained analogously to known compounds such as are described, for example, in German Offenlegungsschriften Nos. 2,456,864, 2,647,452, 2,654,058 and 2,656,769, polyalkylpiperidine spiro compounds being used as the starting materials. The latter are known, for example, from U.S. Pat. Nos. 3,705,126, 3,790,525, 3,859,293 and 3,941,744 and from German Offenlegungsschriften Nos. 2,606,026 and 2,634,957. If individual members of them should still be novel, they can be obtained analogously to the known compounds. The last stage of the synthesis is either a direct esterification (acid+alcohol or acid chloride+alcohol), a transesterification or an amidation.

Typical representatives of compounds of the formula I are listed in Table I below, and of compounds of the formula II in Table II below.

TABLE I

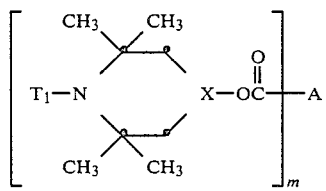

| Stabilizer No. | $T_1$ | X | m | A |
|---|---|---|---|---|
| 1 | $CH_3CO$— | ![](O—CH—CH2— / C / O—CH2) | 1 | $+CH_2\!\!\rightarrow_2$—phenyl with 2,6-di-$C(CH_3)_3$ and 4-OH |
| 2 | $CH_3$— | ![](O—CH—CH2— / C / O—CH2) | 1 | $+CH_2\!\!\rightarrow_2$—phenyl with 2,6-di-$C(CH_3)_3$ and 4-OH |
| 3 | $CH_2$=CH—CO— | ![](O—CH—CH2— / C / O—CH2) | 1 | $+CH_2\!\!\rightarrow_2$—phenyl with 2,6-di-$C(CH_3)_3$ and 4-OH |

TABLE I-continued $$\left[ T_1-N \underset{CH_3 \; CH_3}{\overset{CH_3 \; CH_3}{\diamondsuit}} X-O\overset{O}{\underset{\|}{C}}-A \right]_m$$

| Stabilizer No. | T₁ | X | m | A |
|---|---|---|---|---|
| 4 | CH₃CO— | (acetal with C₂H₅, O-CH₂ groups) | 1 | —(CH₂)₂—C₆H₂(C(CH₃)₃)₂—OH |
| 5 | CH₂=CH—CO— | (acetal with C₂H₅, O-CH₂ groups) | 1 | —(CH₂)₂—C₆H₂(C(CH₃)₃)₂—OH |
| 6 | CH₂=CH—CH₂— | (acetal with C₂H₅, O-CH₂ groups) | 1 | —(CH₂)₂—C₆H₂(C(CH₃)₃)₂—OH |
| 7 | CH₂=CH—CO— | (hydantoin with N—(CH₂)₂) | 1 | —(CH₂)₂—C₆H₂(C(CH₃)₃)₂—OH |
| 8 | CH₂=CH—CO— | (hydantoin with N—(CH₂)₃) | 1 | —(CH₂)₂—C(CH₃)(C₆H₄-4-C(CH₃)₃)(C₆H₃-3-C(CH₃)₃-4-OH) |
| 9 | CH₂=CH—CO— | (hydantoin with N—(CH₂)₃) | 1 | —C₆H₃(C(CH₃)₃)₂—OH |

TABLE I-continued

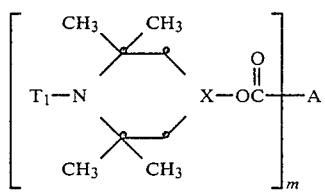

| Stabilizer No. | T₁ | X | m | A |
|---|---|---|---|---|
| 10 | CH₃CO— | (dioxolane with -CH-CH₂-/-O-CH₂-) | 1 | -CH[3,5-di-tert-butyl-4-hydroxyphenyl]₂ |
| 11 | (C₂H₅)₂NCO— | (dioxolane -O-CH₂/-O-CH₂ linked to -C(CH₃)(C₂H₅)-CH₂-) | 1 | -CH[3,5-di-tert-butyl-4-hydroxyphenyl]₂ |
| 12 | (CH₃)₃C, HO-C₆H₂-(CH₃)₃C, -(CH₂)₂COO-(CH₂)₂- | (dioxolane with -CH-CH₂-/-O-CH₂-) | 1 | -(CH₂)₂-[3,5-di-tert-butyl-4-hydroxyphenyl] |
| 13 | (C₂H₅)₂—NCO— | (dioxolane with -CH-CH₂-/-O-CH₂-) | 1 | -(CH₂)₂-[3,5-di-tert-butyl-4-hydroxyphenyl] |
| 14 | CH₃— | (dioxolane with -CH-CH₂-/-O-CH₂-) | 1 | -(CH₂)₂-[3-tert-butyl-4-hydroxyphenyl] |

TABLE I-continued

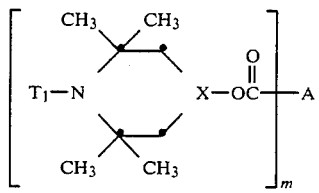

| Stabilizer No. | $T_1$ | X | m | A |
|---|---|---|---|---|
| 15 | 3,5-di-tert-butyl-4-hydroxyphenyl-COO— | ![structure with O-CH-CH2 / C(CH3)2 / O-CH2] | 1 | 3,5-di-tert-butyl-4-hydroxyphenyl |
| 16 | 3,5-di-tert-butyl-4-hydroxyphenyl-COO-(CH2)2— | ![structure with O-CH-CH2 / C(CH3)2 / O-CH2] | 1 | 3,5-di-tert-butyl-4-hydroxyphenyl |
| 17 | CH3CO— | ![structure with C=O, N-(CH2)2, NH-C-(CH2)11] | 1 | -(CH2)2-(3,5-di-tert-butyl-4-hydroxyphenyl) |
| 18 | HO— | ![structure with O-CH2 / C(CH3) / O-CH2, CH2-C-C2H5] | 1 | -(CH2)-(3,5-di-tert-butyl-4-hydroxyphenyl) |
| 19 | CH3— | ![structure with O-CH-CH2 / C(CH3)2 / O-CH2] | 1 | -(CH2)2-C(CH3)(3-tert-butyl-4-hydroxyphenyl)(3-tert-butyl-4-hydroxyphenyl) |
| 20 | 3,5-di-tert-butyl-4-hydroxyphenyl-C(CH3)(3-tert-butyl-4-hydroxyphenyl)-(CH2)2-COO-(CH2)2— | ![structure with O-CH-CH2 / C(CH3)2 / O-CH2] | 1 | -(CH2)2-C(CH3)(3-tert-butyl-4-hydroxyphenyl)(3-tert-butyl-4-hydroxyphenyl) |

TABLE I-continued

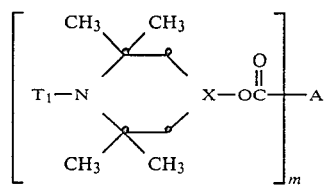

| Stabilizer No. | T₁ | X | m | A |
|---|---|---|---|---|
| 21 | 3,5-di-tert-butyl-4-hydroxyphenyl-(CH₂)₂COO(CH₂)₂- | -C(CH₃)(O-CH₂)₂C(CH₂-)(C₂H₅)- | 1 | -(CH₂)₂-(3,5-di-tert-butyl-4-hydroxyphenyl) |
| 22 | 3,5-di-tert-butyl-4-hydroxyphenyl-(CH₂)₂COO(CH₂)₂- | -C(CH₃)(O-CH)(O-CH₂)CH₂- | 1 | -(CH₂)₂-(3,5-di-tert-butyl-4-hydroxyphenyl) |
| 23 | CH₃CO— | -C(CH₃)(O-CH)(O-CH₂)CH₂- | 2 | -C(CH₃)[CH₂-(3,5-di-tert-butyl-4-hydroxyphenyl)]₂ |
| 24 | CH₃CO— | -C(CH₃)(O-CH₂)₂C(CH₂-)(C₂H₅)- | 2 | -C(C₄H₉)[CH₂-(3,5-di-tert-butyl-4-hydroxyphenyl)] |
| 25 | CH₃— | hydantoin-like: -C(CH₃)(C(=O)-N(-(CH₂)₂-))(NH-C=O)- | 2 | -C(C₄H₉)[CH₂-(3,5-di-tert-butyl-4-hydroxyphenyl)] |

TABLE I-continued
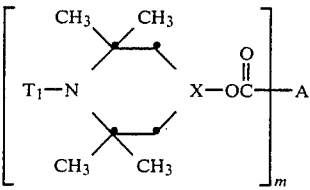
| Stabilizer No. | T₁ | X | m | A |
|---|---|---|---|---|
| 26 | $CH_3-$ | 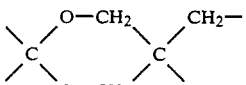 | 2 | 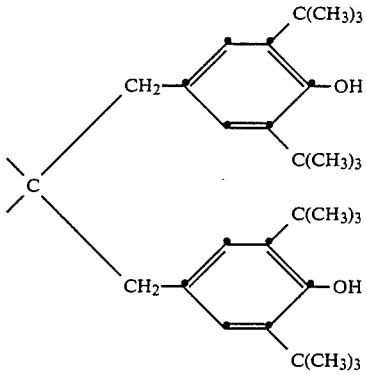 |
| 27 | $CH_3-$ | 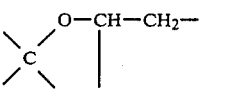 | 2 | 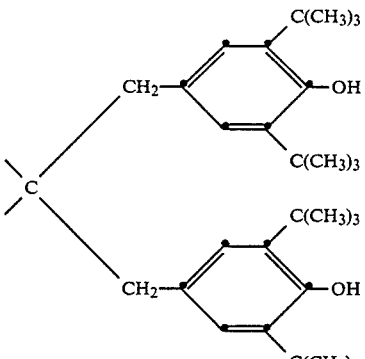 |
| 28 | $CH_3CO-$ | 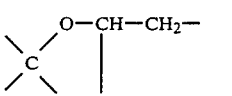 | 2 | 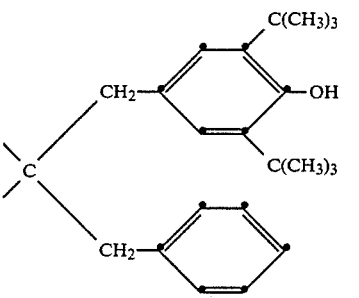 |

TABLE II

| Stabilizer No. | A | m | W |
|---|---|---|---|
| 29 | 3,5-di-tert-butyl-4-hydroxyphenyl-(CH₂)₂— | 1 | $-C(CH_3)_2-O-CH_2-C(-)(-)-CH_2-O-$ (spiro dioxolane) |
| 30 | 3,5-di-tert-butyl-4-hydroxyphenyl-(CH₂)₂— | 1 | spiro ring with C=O-NH and O-C-(CH₂)₁₁ |
| 31 | 3,5-di-tert-butyl-4-hydroxyphenyl— | 1 | $-O-CH-CH_2OSO_2-C_6H_4-CH_3$ dioxolane |
| 32 | 3,5-di-tert-butyl-4-hydroxyphenyl-(CH₂)₂— | 1 | hydantoin-type ring with N-C₈H₁₇ |
| 33 | bis(3,5-di-tert-butyl-4-hydroxybenzyl)C< | 2 | hydantoin-type ring with NH |

Further typical representatives of compounds of the formula II are the stabilisers

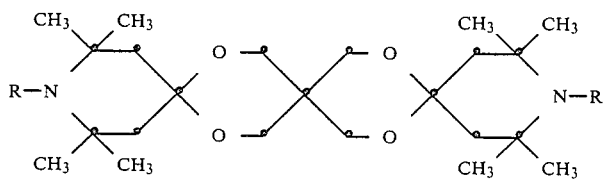

34

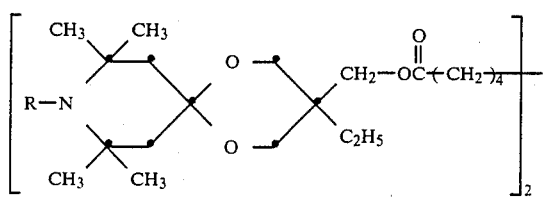

35

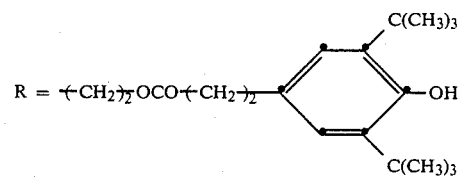

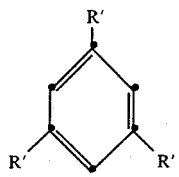

36

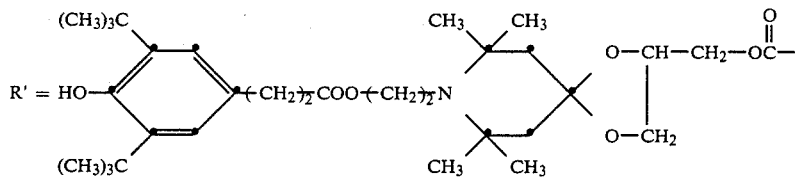

The stabilizers of the formula I or II can be incorporated in a known manner into a photographic material on their own or together with other compounds.

As a rule, the stabilizers are incorporated into the photographic material on their own or together with other compounds, particularly with colour couplers, in the form of a dispersion, this dispersion either containing no solvent or containing high-boiling or low-boiling solvents or a mixture of such solvents. A further suitable mode of incorporation consists in incorporating the stabilizers on their own or together with further compounds, together with a polymer in the form of a latex, into the photographic material.

The dispersions are then used to prepare the layers of colour-photographic recording materials. These layers can be, for example, intermediate layers or protective layers, but particularly light-sensitive (blue-, green- and red-sensitive) silver halide emulsion layers, in which the blue-green (cyan) dyes, purple (magenta) dyes and yellow dyes are formed from the appropriate colour couplers when the exposed recording material is developed.

The silver halide layers can contain any desired colour couplers, particularly blue-green, purple and yellow couplers, which are used to form the said dyes and thus the dye images.

Since the substrate affects the action and stability of the compounds of the formula I or II, preferred substrates (solvents or polymers) are those which, together with these compounds, produce the best possible stability in the compounds to be stabilized.

As a rule, the stabilizers are incorporated into layers containing, in addition, a silver halide dispersion which has been prepared and sensitized by conventional methods. They can, however, also be present in layers which are adjacent to layers containing silver halide.

The photographic materials according to the invention have a conventional composition and contain conventional components. It is preferable, however, to have a composition and components which enhance, or at least do not adversely affect, the activity of the stabilizers of the formula I or II.

In the photographic recording material according to the present invention, the stabilizers of the formula I and II can be combined in the same layer not only with the colour couplers, but also, in addition, with ultraviolet absorbers or other light stabilisers.

If the diffusion transfer method is used, the stabilizer can also be incorporated in a receiving layer.

The colour-photographic materials according to the invention can be processed in a known manner. Furthermore, they can be treated in the course of, or after, processing in a manner which increases their stability further, for example by treatment in a stabilizer bath or by the application of a protective coating.

In certain cases, the stabilizers which can be employed in accordance with the invention are also suitable for protecting colour-photographic layers in which the dyes are directly incorporated in the emulsion and the image is produced by selective bleaching.

The amount of the stabilizer or stabilizers can vary within wide limits and is approximately within the range from 1 to 2,000 mg, preferably 100 to 800 and, in particular, 200–500 mg, per m² of the layer in which it (they) is (are) incorporated.

If the photographic material contains an agent which absorbs UV radiation, the latter can be present together with the stabilizer in one layer or can also be present in an adjacent layer. The amount of the UV absorber, or of UV absorbers, can vary within wide limits and is approximately within the range from 200 to 2,000 mg, preferably 400 to 1,000 mg, per m² of the layer in which it (they) is (are) incorporated. Examples of ultraviolet absorbers are compounds of the benzophenone, acrylonitrile, thiazolidone, benztriazole, oxazole, thiazole and imidazole type.

The colour images obtained with the recording material according to the invention by exposure and development have a very good light-fastness towards visible and ultraviolet light. The compounds of the formulae I and II are virtually colourless, so that no discolouration of the images results; in addition they are readily compatible with the customary photographic additives present in the individual layers. By virtue of their good activity, it is possible to reduce the quantity of them which is employed and thus to prevent them from being precipitated or crystallising out if they are incorporated as an organic solution into the aqueous binder emulsions used for the preparation of photographic layers. The individual processing stages required, after the exposure of the photographic recording material, for the production of the colour images are not adversely affected by the stabilisers. Furthermore, the so-called formation of abrasion fogging which frequently occurs with blue-sensitive emulsions is substantially repressed. This can occur, for example, if mechanical stresses, for example twisting, bending or rubbing, are exerted on photographic materials (silver halide emulsion layers located on a base composed of natural or synthetic materials) while they are being prepared or treated before being developed. (T. H. James, The Theory of the Photographic Process, 4th edition, Macmillan, New York, N.Y. 1977, pages 23 et seq and 166 et seq).

USE EXAMPLES 0.087 g of the yellow coupler of the formula

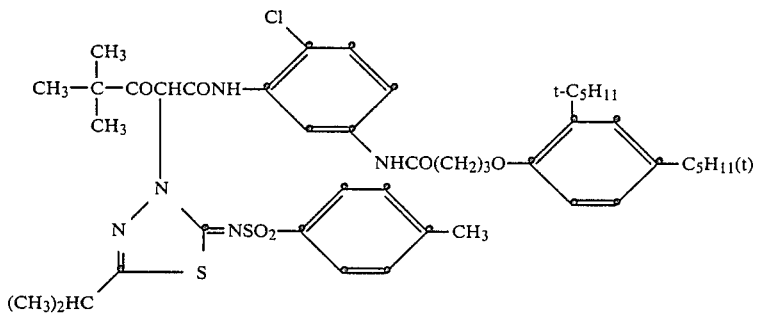

and 0.026 g of one of the light stabilizers indicated in the Tables below are dissolved in 2.0 ml of a mixture of tricresyl phosphate and ethyl acetate (1.5 g in 100 ml). 7.0 ml of a 6% gelatine solution, 0.5 ml of an 8% solution of the wetting agent of the formula

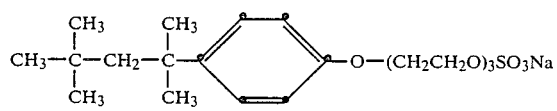

in isopropanol/water (3:4) and 0.5 ml of water are added to this solution, and the mixture is emulsified by ultrasonic means at an input of 100 watts for 5 minutes.

2.0 ml of a silver bromide emulsion having a silver content of 6.0 g per liter, 0.7 ml of a 1% aqueous solution of the hardener of the formula

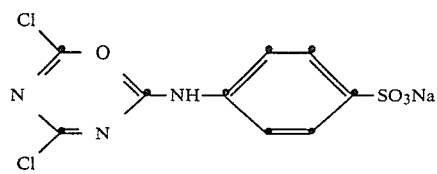

and 3.8 ml of water are added to 2.5 ml of the emulsion thus obtained, the pH of the mixture is adjusted to a value of 6.5 and it is coated onto a subbed, plastic-coated white sheet of paper, mounted on a glass plate.

After the mixture has solidified, it is dried at room temperature in a circulating air drying cabinet.

After 7 days, samples cut to dimensions of 35×180 mm are exposed at 3,000 Lux.second behind a stepped wedge and are then processed by the kodak ektaprint 2-stage ® process.

The yellow wedges thus obtained are irradiated at a total of 42 kjoules/cm² in an Atlas Weather-ometer using a 2,500 watt xenon lamp (a comparison sample contains no light stabiliser).

The loss of colour density thereby occasioned is determined by measuring the colour density at $\lambda_{max}$ using a densitometer (TR ®924 A made by Macbeth).

The results are shown in the Table below.

| Light stabilizer No. | Percentage loss of density from maximum (Reflectance) |
| --- | --- |
| — | 36 |
| 8 | 15 |
| 9 | 15 |
| 16 | 16 |
| 20 | 15 |

What we claim is:

1. A colour-photographical recording material which, in at least one light-sensitive silver halide emulsion layer, one intermediate layer and/or one protective layer, contains, as a stabilizer, a light stabilizing amount of at least one polyalkylpiperidine compound, wherein the polyalkylpiperidine compound has one of the formulae I or II

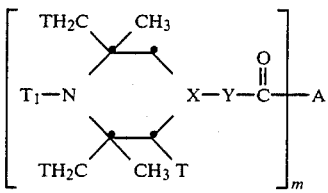
(I)

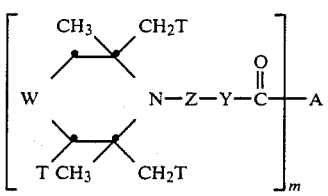
(II)

in which m is 1 or 2, if m=1, A is a group of the formula

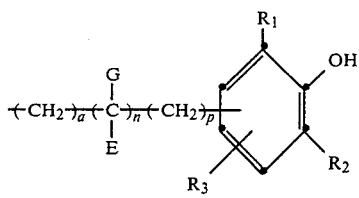

and, if m=2, A is a group of the formula

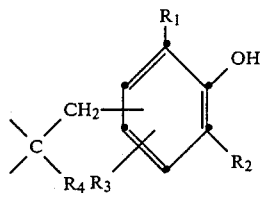

in which $R_1$ is hydrogen, $C_1$–$C_{12}$-alkyl, $C_5$–$C_8$-cycloalkyl, $C_7$–$C_9$-phenylalkyl, phenyl or $C_7$–$C_{10}$-alkylphenyl, $R_2$ is $C_1$–$C_8$-alkyl, $C_5$–$C_8$-cycloalkyl, $C_7$–$C_9$-phenylalkyl, phenyl or $C_7$–$C_{10}$-alkylphenyl, $R_3$ is hydrogen or methyl, $R_4$ is hydrogen, $C_1$–$C_{12}$-alkyl, allyl, benzyl, cyclohexyl or a group

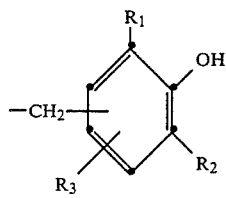

G is hydrogen or a group

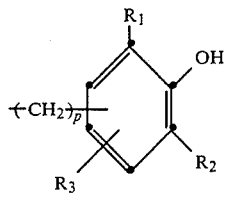

E is hydrogen, methyl, —CN, —$COR_5$ or —$COOR_5$, $R_5$ being $C_1$–$C_8$-alkyl or $C_3$–$C_4$-alkoxyalkyl, and n and p independently of one another are 0 or 1 and a is 0, 1 or 2, y is —O— or —$N(R_6)$—, $R_6$ being hydrogen, $C_1$–$C_{18}$-alkyl, $C_3$–$C_{12}$-alkenyl, $C_5$–$C_8$-cycloalkyl, phenyl, $C_7$–$C_{14}$-alkaryl, $C_7$–$C_{14}$-aralkyl or $C_3$–$C_4$ alkoxyalkyl, Z is a group

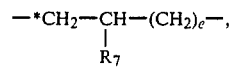

in which $R_7$ is hydrogen, methyl, ethyl, phenoxymethyl, phenyl or —$OR_8$, but is only —$OR_8$ if e is 1, and in which $R_8$ is hydrogen or —COL, L is $C_1$–$C_4$-alkyl, e is 0 or 1 and the *C is attached at the piperidine nitrogen, T is hydrogen or methyl, $T_1$ is hydroxyl, $C_1$–$C_{12}$-alkyl, $C_3$–$C_6$-alkenylmethyl or $C_3$–$C_4$-alkynylmethyl and $C_7$–$C_{14}$-aralkyl, glycidyl, $C_1$–$C_4$-alkyl which is substituted by halogen, cyano, —$COOR_9$ or —$CON(R_{10})(R_{11})$, a group —$COR_{12}$, —$COOR_9$ or —$CON(R_{10})(R_{11})$ or a group —$CH_2$—$CH(R_{13})$—$OR_{14}$, —$SOR_{15}$, —$SO_2R_{15}$, —$OR_9$ or —$OOCR_{12}$ in which $R_9$ is $C_1$–$C_{12}$-alkyl, allyl, cyclohexyl or benzyl, $R_{10}$ is $C_1$–$C_{12}$-alkyl, allyl, cyclohexyl, benzyl, phenyl or $C_7$–$C_{10}$-alkylphenyl and $R_{11}$ is hydrogen, $C_1$–$C_{12}$-alkyl, allyl, cyclohexyl or benzyl, or $R_{10}$ and $R_{11}$, together with the N atom to which they are attached, form a 5-membered or 6-membered heterocyclic ring, $R_{12}$ is hydrogen, $C_1$–$C_{12}$-alkyl, $C_2$–$C_6$-alkenyl, chloromethyl, $C_5$–$C_8$-cycloalkyl, $C_7$–$C_{14}$-aralkyl, phenyl, $C_7$–$C_{10}$-alkylphenyl or phenyl, phenylmethyl or phenylethyl which is substituted by one or two $C_1$–$C_4$-alkyl groups and by one hydroxyl group, $R_{13}$ is hydrogen, $C_1$–$C_4$-alkyl, $C_3$–$C_4$-alkoxyalkyl, phenyl or phenoxymethyl, $R_{14}$ is hydrogen, $C_1$–$C_{12}$-alkyl or a group —$COR_{12}$ or —$CON(R_{10})(R_{11})$ and $R_{15}$ is $C_1$–$C_{12}$-alkyl, phenyl or $C_7$–$C_{10}$-alkylphenyl, or $T_1$ is a group of the formula

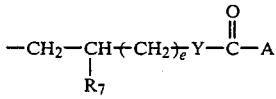

or of the formula

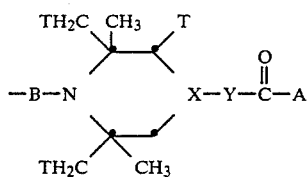

in which B is a group $C_rH_{2r}$ in which r is an integer of from 2 to 12, or is $C_4$–$C_8$-alkenylene, $C_4$–$C_8$-alkynylene, phenylene, xylylene, bitolylene, $C_5$–$C_{12}$-cycloalkylene or a group —CONH—$B_1$—NECO— in which $B_1$ is a group $C_rH_{2r}$, phenylene, naphthylene, tolylene or a group of the formulae

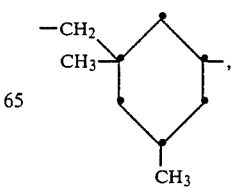

-continued

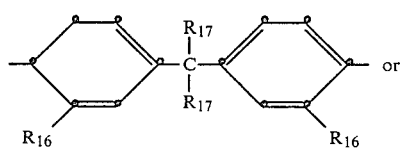 or

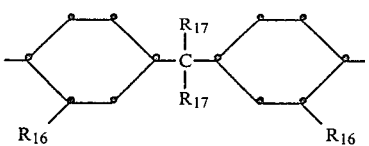

in which $R_{16}$ is hydrogen or methyl and $R_{17}$ is hydrogen, methyl or ethyl, X is one of the groups

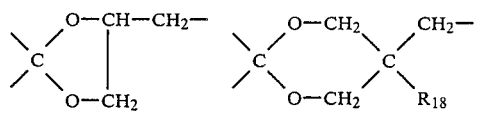

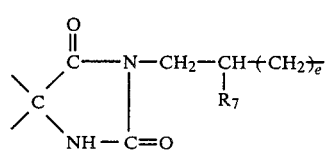

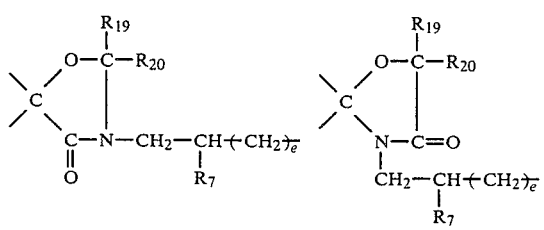

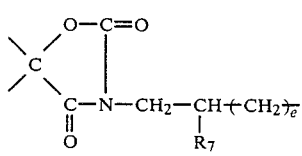

and W is one of the groups

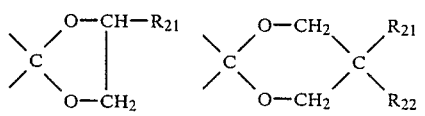

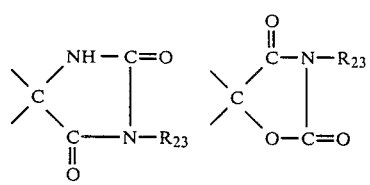

-continued

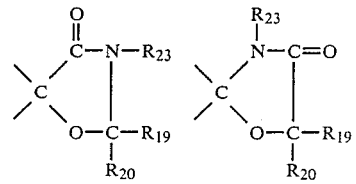

in which $R_{18}$ is methyl or ethyl, $R_{19}$ is hydrogen, $C_1$–$C_{12}$-alkyl, $C_5$–$C_8$-cycloalkyl or $C_7$–$C_{14}$-aralkyl, $R_{20}$ is $C_1$–$C_{12}$-alkyl, $C_5$–$C_8$-cycloalkyl or phenyl, or $R_{19}$ and $R_{20}$, together with the C atom to which they are attached, form a $C_5$–$C_{12}$ cycloalkane or alkylcycloalkane ring, $R_{21}$ is hydrogen, $C_1$–$C_{12}$-alkyl or a group of the formula —$CH_2$—$OCOR_{24}$ in which $R_{24}$ is hydrogen, $C_1$–$C_4$-alkyl, $C_2$–$C_6$-alkenyl, cyclohexyl, phenyl, benzyl or chloromethyl, or is a group —$CH_2$—$O$—$SO_2R_{27}$ in which $R_{27}$ is methyl, phenyl or p-tolyl, or is one of the groups

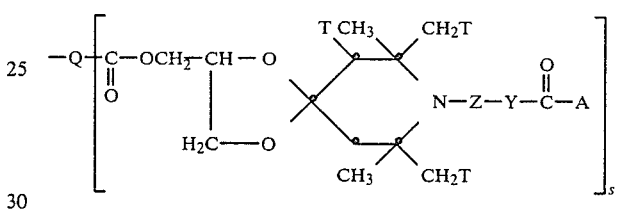

or

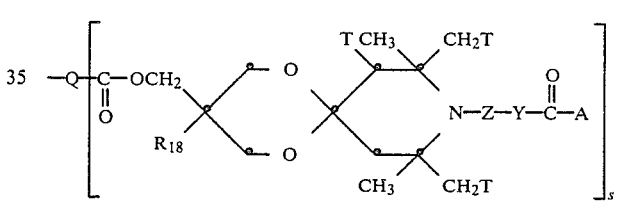

in which s is 1, 2 or 3, and, if s=1, Q is as defined above for B, if s=2, Q is a trivalent radical of the formulae

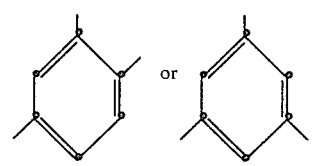 or and, if s=3, Q is a tetravalent radical of the formulae

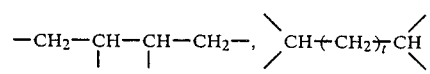

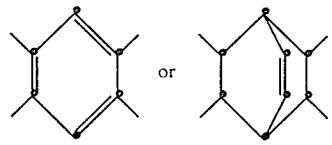 or in which t is an integer of 1 to 8, and $R_{21}$ additionally is also a group of the formula —$CH_2O$—$SOR_{25}$ in which $R_{25}$ is $C_1$–$C_4$-alkyl, p-tolyl or phenyl, or is a group of the formula —CH₂—CO—NHR₂₆ in which R₂₆ is hydrogen or C₁-C₄-alkyl, R₂₂ is hydrogen or C₁-C₄-alkyl and R₂₃ is hydrogen, C₁-C₁₂-alkyl, C₃-C₄-alkoxyalkyl, C₅-C₈-cycloalkyl, allyl or benzyl, and, if m is 1, W can additionally also be a group of the formula

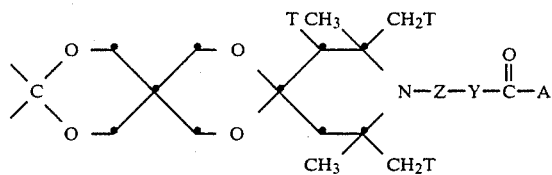

the radicals and symbols mentioned several times always being as defined initially.

2. A colour-photographic recording material according to claim 1, which contains, as a stabilizer, at least one polyalkylpiperidine compound having one of the formulae III or IV

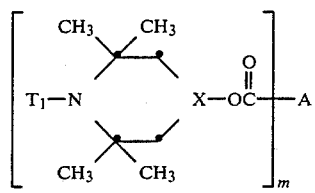

(III)

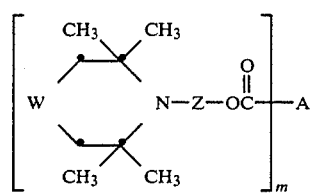

(IV)

in which m is 1 or 2, if m=1, A is a group of the formula

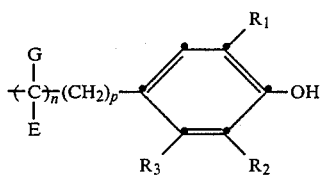

and, if m=2, A is a group of the formula

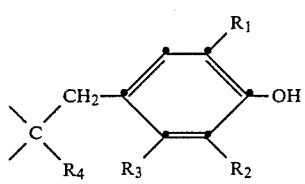

in which $R_1$ is $C_1$-$C_4$-alkyl, $R_2$ is hydrogen or $C_1$-$C_4$-alkyl, $R_3$ is hydrogen or methyl, $R_4$ is hydrogen, $C_1$-$C_4$-alkyl or a group

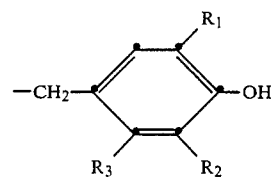

G is hydrogen or a group

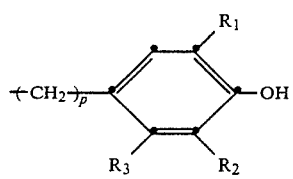

E is hydrogen, methyl, —CN or —COCH₃ and n and p independently of one another are 0 or 1, Z is a group

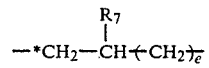

in which $R_7$ is hydrogen, methyl, ethyl, phenoxymethyl and phenyl, e is 0 or 1 and the *C is attached at the piperidine nitrogen, $T_1$ is hydroxyl, $C_1$-$C_4$-alkoxy, acetoxy, $C_1$-$C_4$-alkyl, $C_3$-$C_4$-alkenylmethyl, propargyl, glycidyl, benzyl, methyl or ethyl which is substituted by —COOR₉, a group —COR₁₂, —COOR₉ or —CON(R₁₀) (R₁₁), or a group —CH₂—CH(R₁₃)—OR₁₄ in which R₉ is C₁-C₈-alkyl, allyl or cyclohexyl, R₁₀ is C₁-C₁₂-alkyl, cyclohexyl or phenyl, R₁₁ is hydrogen or C₁-C₁₂-alkyl, or R₁₀ and R₁₁, together with the N atom to which they are attached, form a 6-membered heterocyclic ring, R₁₂ is C₁-C₁₂-alkyl, C₂-C₄-alkenyl, cyclohexyl, benzyl, phenyl or 2-(3,5-ditert.-butyl-4-hydroxyphenyl)-ethyl, R₁₃ is hydrogen, methyl or phenyl and R₁₄ is hydrogen, C₁-C₄-alkyl or a group —COR₁₂ or —CON(R₁₀)(R₁₁), or T₁ is a group of the formula

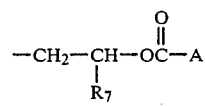

or of the formula

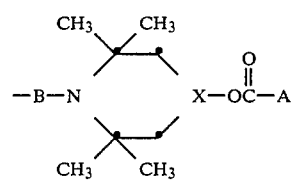

ps in which B is a group —(CH₂)ᵣ— or —CONH—(CH₂)ᵣ—NCHO— in which r is an integer of 2 to 8, or is C₄-C₈-alkenylene, xylylene or bitolylene, X is one of the groups

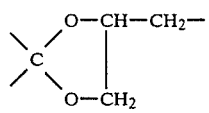 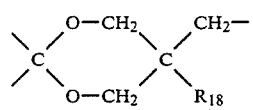

-continued

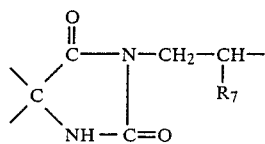

and W is one of the groups

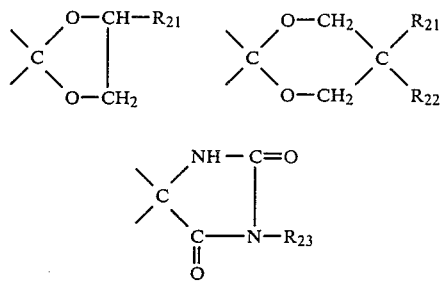

in which $R_{18}$ is methyl or ethyl, $R_{21}$ is hydrogen, $C_1$–$C_8$-alkyl, a group of the formula —$CH_2$—$OCOR_{24}$ in which $R_{24}$ is $C_1$–$C_4$-alkyl, allyl, phenyl or benzyl, or a group of the formula —$CH_2O$—$SO_2R_{27}$ in which $R_{27}$ is methyl, phenyl or p-tolyl, $R_{22}$ is hydrogen, methyl or ethyl and $R_{23}$ is hydrogen, $C_1$–$C_8$-alkyl, cyclohexyl, allyl or benzyl, and, if m is 1, W can additionally also be a group of the formula

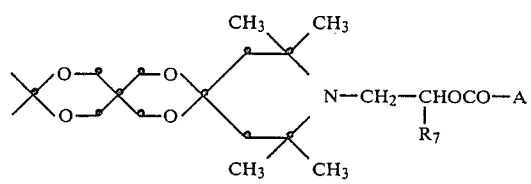

the radicals and symbols mentioned several times in this claim alway being as defined initially in this claim.

3. A colour-photographic recording material according to claim 1, which contains, as a stabilizer, at least one polyalkylpiperidine compound of the formula III in which m is 1 or 2, if m=1, A is a group of the formula

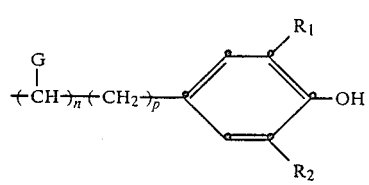

and, if m=2, A is a group of the formula

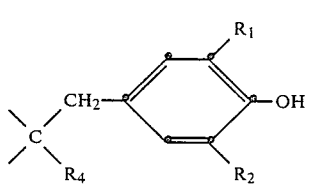

in which $R_1$ is hydrogen, methyl or tert.-butyl, $R_2$ is methyl or tert.-butyl, $R_4$ is hydrogen, $C_1$–$C_4$-alkyl or a group

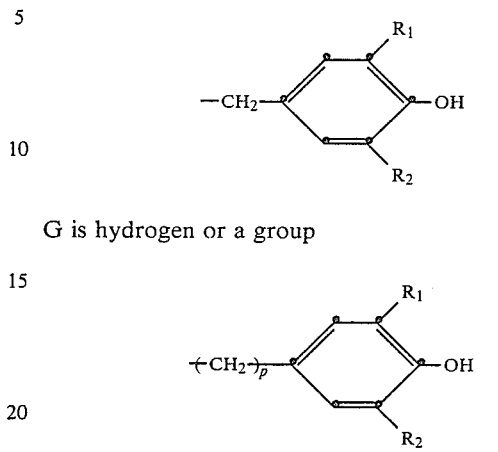

G is hydrogen or a group

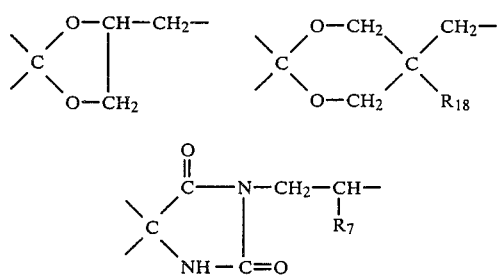

n and p independently of one another are 0 or 1, and $T_1$ is methoxy, methyl, allyl, benzyl, acetyl, acryloyl or a group —$CON(R_{10})(R_{11})$, $R_{10}$ being $C_1$–$C_4$-alkyl, cyclohexyl or phenyl and $R_{11}$ being hydrogen or $C_1$–$C_4$-alkyl, or $T_1$ is a group —$CH_2CH_2$—$OCO$—A, X is one of the groups

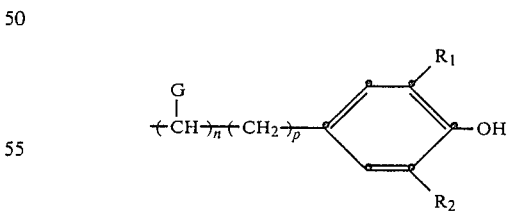

in which $R_7$ is hydrogen, methyl or phenyl and $R_{18}$ is methyl or ethyl, the radicals mentioned several times in this claim always being as defined initially in this claim.

4. A colour-photographic recording material according to claim 1, which contains, as a stabilizer, at least one polyalkylpiperidine compound of the formula IV in which m is 1 or 2, if m—1, A is a group of the formula

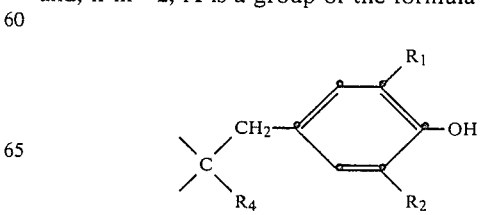

and, if m=2, A is a group of the formula in which $R_1$ is hydrogen, methyl or tert.-butyl, $R_2$ is methyl or tert.-butyl, $R_4$ is hydrogen, $C_1$–$C_4$-alkyl or a group

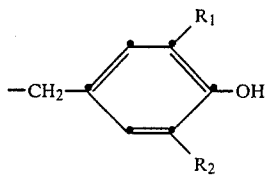

G is hydrogen or a group

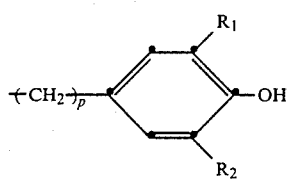

n and p independently of one another are 0 or 1, Z is a group

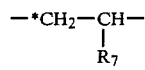

in which $R_7$ is hydrogen, methyl or phenyl and the *C is attached at the piperidine nitrogen, $T_1$ is methoxy, methyl, allyl, benzyl, acetyl, acryloyl or a group —CON($R_{10}$)($R_{11}$), —SOR$_{15}$ or —SO$_2$R$_{15}$, $R_{10}$ being $C_1$–$C_4$-alkyl, cyclohexyl or phenyl, $R_{11}$ being hydrogen or $C_1$–$C_4$-alkyl and $R_{15}$ being methyl, phenyl or p-tolyl, or $T_1$ is a group —CH$_2$CH$_2$OCO—A, W is one of the groups

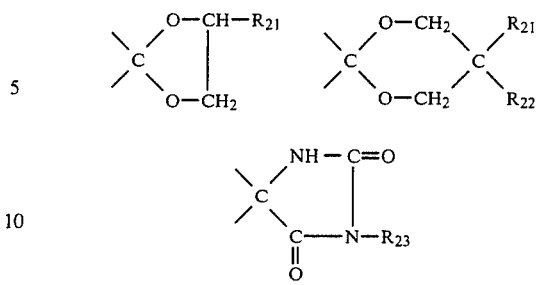

in which $R_{21}$ is hydrogen, $C_1$–$C_8$-alkyl, a group of the formula —CH$_2$—OCOR$_{24}$ in which $R_{24}$ is $C_1$–$C_4$-alkyl, allyl or benzyl, or a group of the formula —CH$_2$O—SO$_2$R$_{27}$ in which $R_{27}$ is methyl, phenyl or p-tolyl, $R_{22}$ is hydrogen, methyl or ethyl and $R_{23}$ is hydrogen, $C_1$–$C_8$-alkyl, allyl or benzyl, and, if m is 1, W can additionally also be a group of the formula

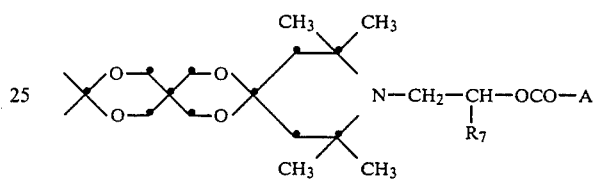

the radicals mentioned several times in this claim always being as defined initially in this claim.

5. A colour-photographic recording material according to claim 1, which contains, as a stabilizer, at least one polyalkylpiperidine compound of the formula V

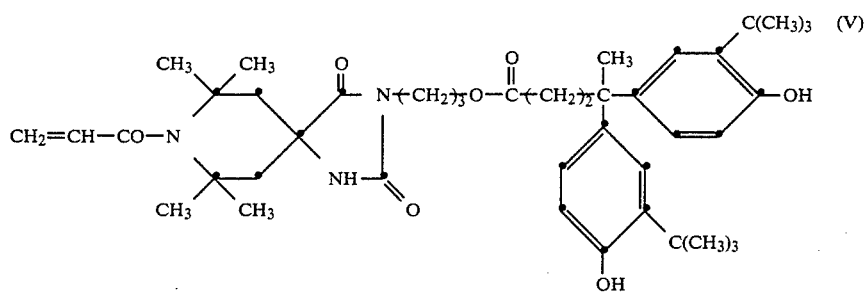

6. A colour-photographic recording material according to claim 1, which contains, as a stabilizer, at least one polyalkylpiperidine compound of the formula VI

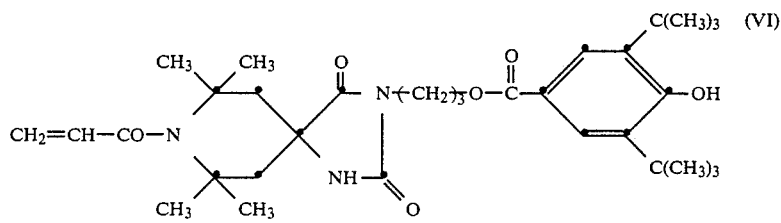

7. A colour-photographic recording material according to claim 1, which contains, as a stabilizer, at least one polyalkylpiperidine compound of the formula VII

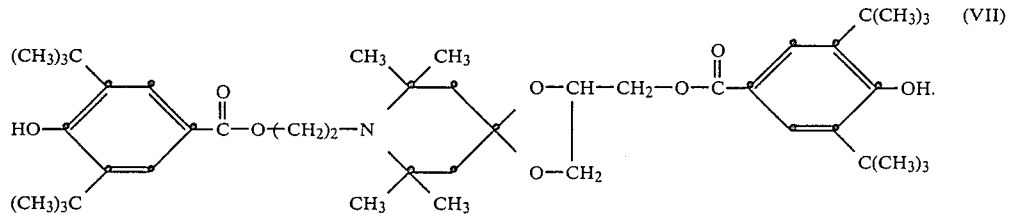

8. A colour-photographic recording material according to claim 1, which contains, as a stabilizer, at least one polyalkylpiperidine compound of the formula VIII

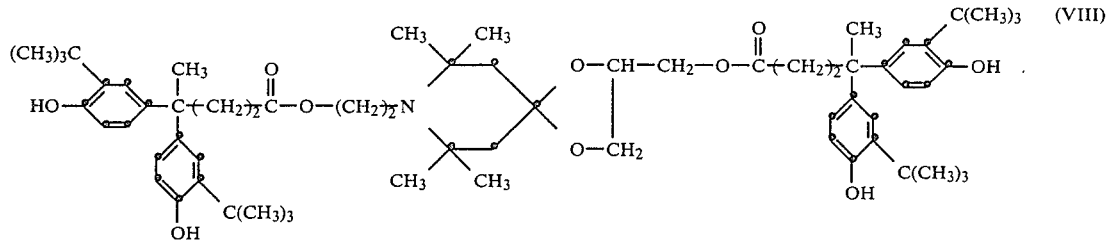

9. A colour-photographic recording material according to claim 1, which contains the stabilizers of the formulae I or II in combination with blue-green, purple and yellow couplers.

10. A colour-photographic recording material according to claim 1, which contains the stabilizers of the formulae I or II in combination with ultraviolet absorbers.

11. A colour-photographic recording material according to claim 10, wherein the ultraviolet absorbers are compounds of the benzophenone, acrylonitrile, thiazolidone, benztriazole, oxazole, thiazole or imidazole type.

12. A colour-photographic recording material according to claim 1, which contains the stabilizers of the formulae I or II in combination with blue-green, purple and yellow couplers and with UV absorbers in the same layer.

13. A colour-photographic recording material according to claim 1, which contains 1 to 2,000 mg of the stabilizer per $m^2$ of the layer into which it has been incorporated.

14. A process for the production of photographic colour images by image-wise exposure and colour development of a colour-photographic recording material according to claim 1.

* * * * *